(12) United States Patent
Smucker et al.

(10) Patent No.: US 7,344,540 B2
(45) Date of Patent: Mar. 18, 2008

(54) PATELLA RESECTION GUIDE

(75) Inventors: Donald M. Smucker, Perrysburg, OH (US); Richard R. Van Zile, Bryan, OH (US)

(73) Assignee: Zimmer, Inc., Warsaw, IN (US)

(*) Notice: Subject to any disclaimer, the term of this patent is extended or adjusted under 35 U.S.C. 154(b) by 456 days.

(21) Appl. No.: 10/373,930

(22) Filed: Feb. 25, 2003

(65) Prior Publication Data

US 2003/0163137 A1 Aug. 28, 2003

Related U.S. Application Data

(60) Provisional application No. 60/359,631, filed on Feb. 26, 2002.

(51) Int. Cl.
*A61F 5/00* (2006.01)

(52) U.S. Cl. ...................................................... 606/87

(58) Field of Classification Search .................. 606/79, 606/80, 82–84, 86, 96
See application file for complete search history.

(56) References Cited

U.S. PATENT DOCUMENTS

| | | | |
|---|---|---|---|
| 4,524,766 A | 6/1985 | Petersen | |
| 4,565,192 A | 1/1986 | Shapiro | |
| 4,566,448 A | 1/1986 | Rohr, Jr. | |
| 4,633,862 A * | 1/1987 | Petersen | 606/80 |
| 4,718,413 A | 1/1988 | Johnson | |
| 4,722,330 A | 2/1988 | Russell et al. | |
| 4,759,350 A | 7/1988 | Dunn et al. | |
| 4,841,975 A | 6/1989 | Woolson | |
| 4,892,093 A | 1/1990 | Zarnowski et al. | |
| 4,935,023 A | 6/1990 | Whiteside et al. | |
| 5,002,547 A | 3/1991 | Poggie et al. | |
| 5,080,675 A | 1/1992 | Lawes et al. | |
| 5,122,144 A | 6/1992 | Bert et al. | |
| 5,180,384 A | 1/1993 | Mikhail | |
| 5,219,362 A | 6/1993 | Tuke et al. | |
| 5,222,955 A | 6/1993 | Mikhail | |
| 5,234,433 A | 8/1993 | Bert et al. | |
| 5,284,482 A | 2/1994 | Mikhail | |
| 5,306,285 A | 4/1994 | Miller et al. | |
| 5,330,533 A | 7/1994 | Walker | |
| 5,342,366 A | 8/1994 | Whiteside et al. | |
| 5,417,694 A | 5/1995 | Marik et al. | |
| 5,417,695 A | 5/1995 | Axelson, Jr. | |
| 5,454,816 A | 10/1995 | Ashby | |
| 5,486,178 A | 1/1996 | Hodge | |
| 5,520,692 A * | 5/1996 | Ferrante | 606/80 |

(Continued)

OTHER PUBLICATIONS

International Search Report in International Application No. PCT/US03/05726 corresponding to this U.S. application.

(Continued)

*Primary Examiner*—Eduardo C. Robert
*Assistant Examiner*—Michael J Araj
(74) *Attorney, Agent, or Firm*—Baker & Daniels LLP

(57) ABSTRACT

A method and apparatus for resectioning a patella without everting it includes a resection guide which grips the patella with gripping members, one of which can also function as an alignment guide for a surgeon using a saw for the resectioning. A sizing/alignment guide engageable with the resection guide is provided for aligning drills and/or reamers used in resectioning. Under one embodiment, a pair of reamers are provided for reaming the patella in two reaming operations.

15 Claims, 13 Drawing Sheets

U.S. PATENT DOCUMENTS

| | | | |
|---|---|---|---|
| 5,520,695 A | 5/1996 | Luckman | |
| 5,536,271 A * | 7/1996 | Daly et al. | 606/80 |
| 5,569,261 A | 10/1996 | Marik et al. | |
| 5,601,563 A | 2/1997 | Burke et al. | |
| 5,609,639 A | 3/1997 | Walker | |
| 5,658,291 A * | 8/1997 | Techiera | 606/80 |
| 5,658,292 A | 8/1997 | Axelson, Jr. | |
| 5,662,656 A | 9/1997 | White | |
| 5,683,397 A | 11/1997 | Vendrely et al. | |
| 5,688,281 A | 11/1997 | Cripe et al. | |
| 5,702,466 A | 12/1997 | Pappas et al. | |
| 5,716,360 A * | 2/1998 | Baldwin et al. | 606/80 |
| 5,716,362 A | 2/1998 | Treacy | |
| 5,720,752 A | 2/1998 | Elliott et al. | |
| 5,749,876 A | 5/1998 | Duvillier et al. | |
| 5,782,920 A | 7/1998 | Colleran | |
| 5,810,831 A | 9/1998 | D'Antonio | |
| 5,830,216 A | 11/1998 | Insall et al. | |
| 5,885,298 A * | 3/1999 | Herrington et al. | 606/88 |
| 5,910,143 A | 6/1999 | Cripe et al. | |
| 5,911,723 A | 6/1999 | Ashby et al. | |
| 5,914,884 A | 6/1999 | Gur et al. | |
| 6,010,509 A * | 1/2000 | Delgado et al. | 606/88 |
| 6,013,081 A | 1/2000 | Burkinshaw et al. | |
| 6,059,831 A | 5/2000 | Braslow et al. | |
| 6,102,954 A | 8/2000 | Albrektsson et al. | |
| 6,159,246 A | 12/2000 | Mendes et al. | |
| 6,174,314 B1 | 1/2001 | Waddell | |
| 7,048,741 B2 | 5/2006 | Swanson | |
| 2004/0162561 A1 | 8/2004 | Marchyn et al. | |

OTHER PUBLICATIONS

International Search Report in International Application No. PCT/US03/05726 corresponding to this U.S. application, Jul. 3, 2003.

* cited by examiner

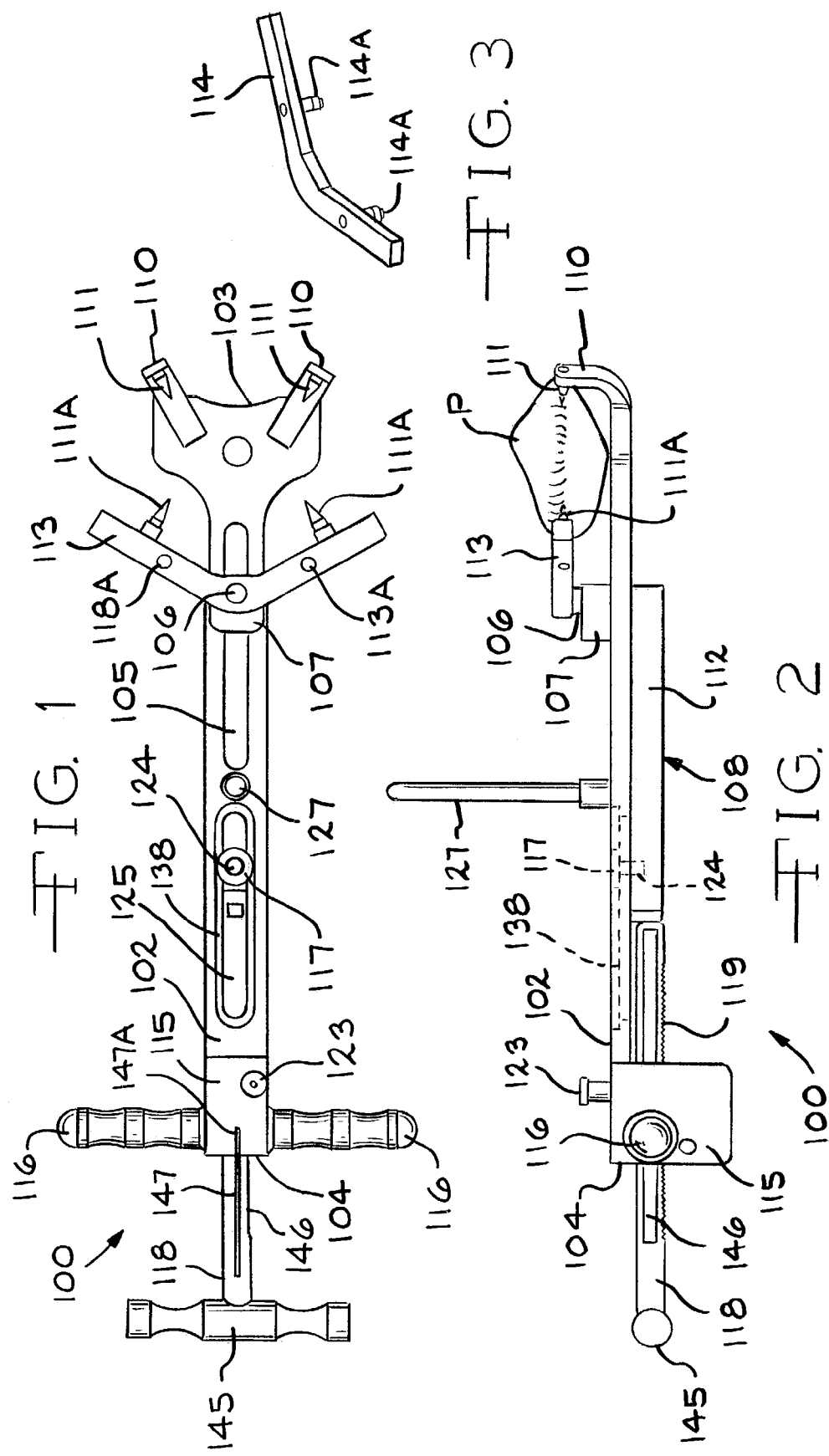

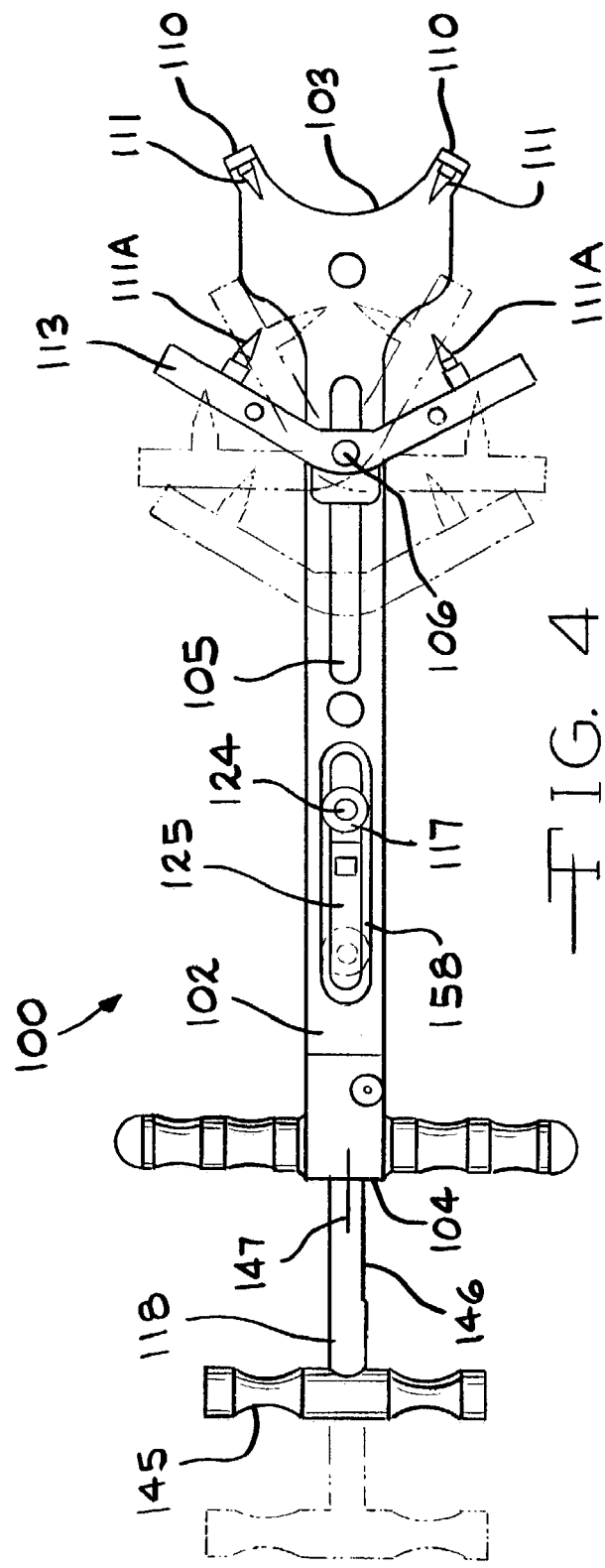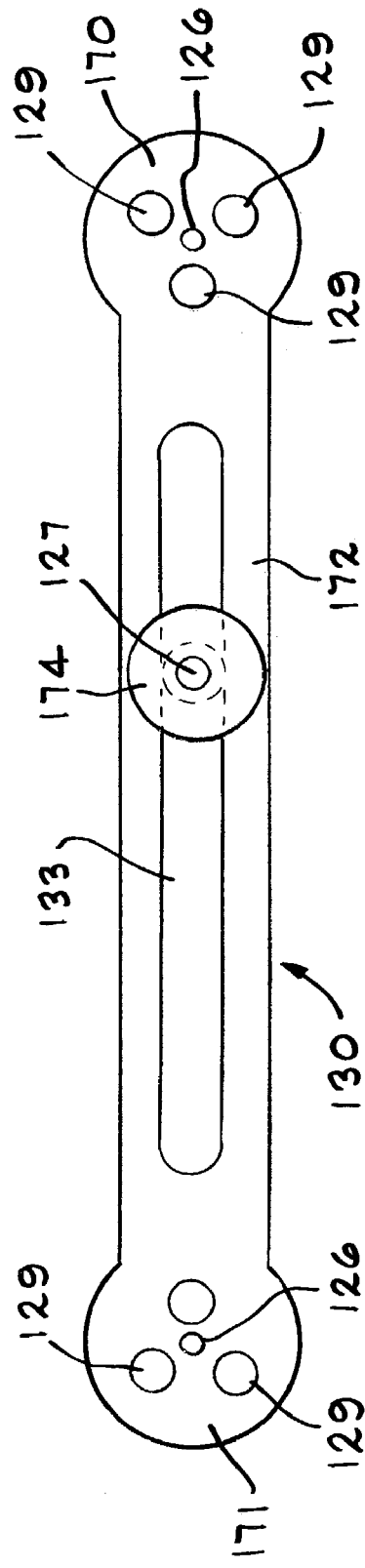

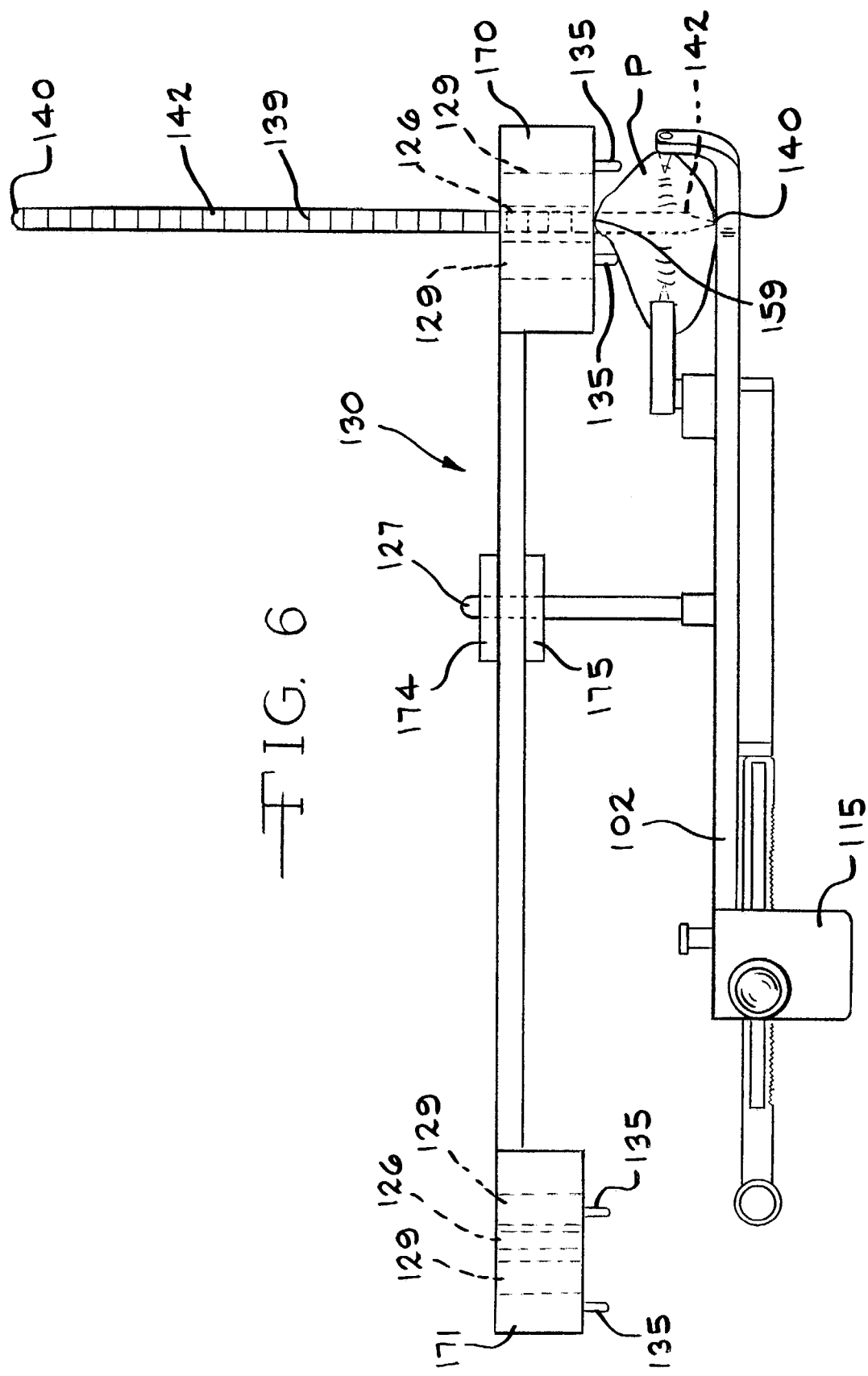

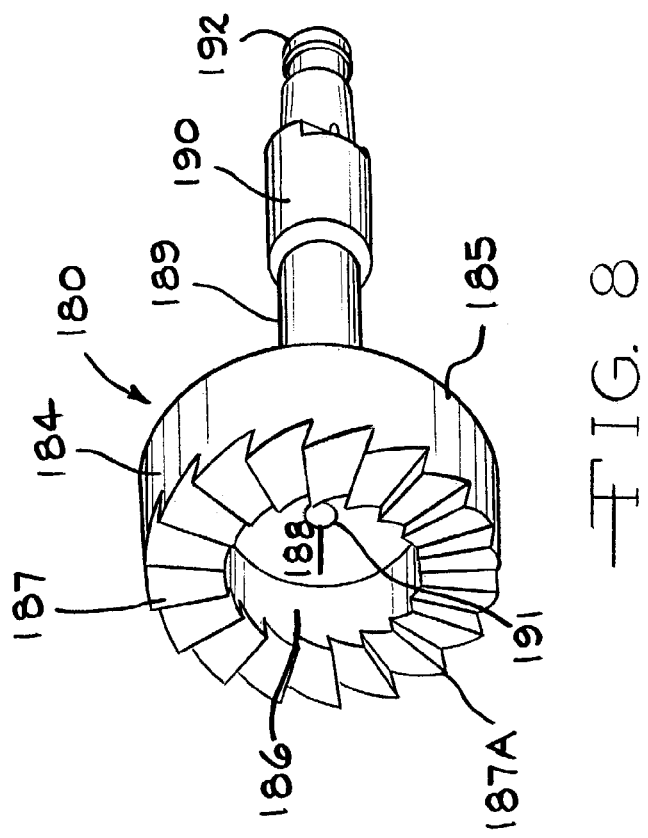
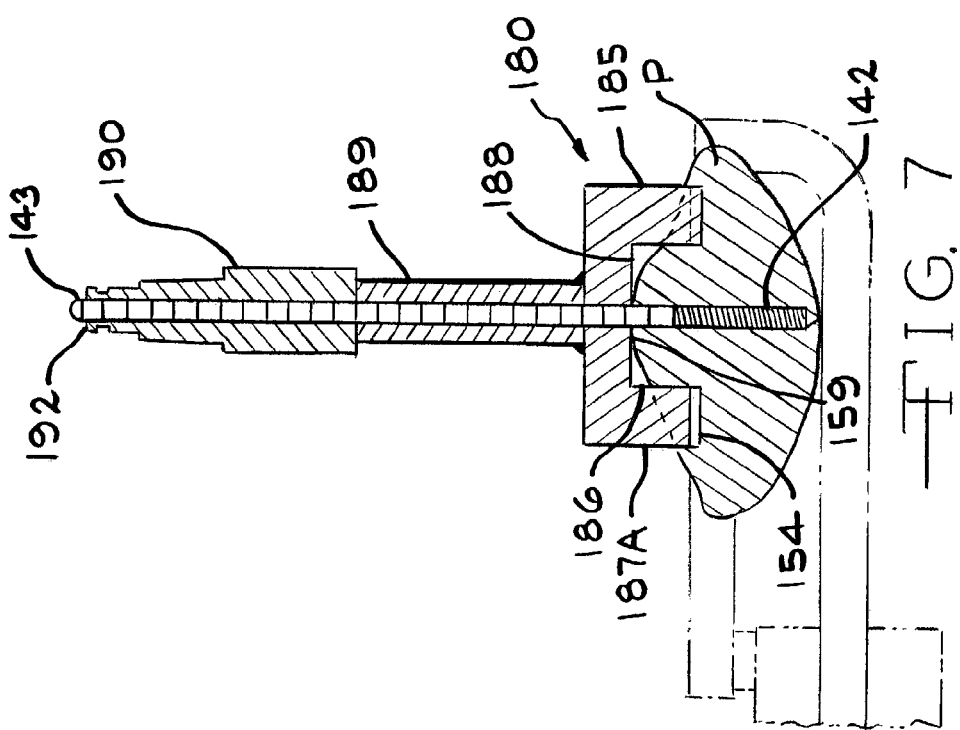
FIG. 8
FIG. 7

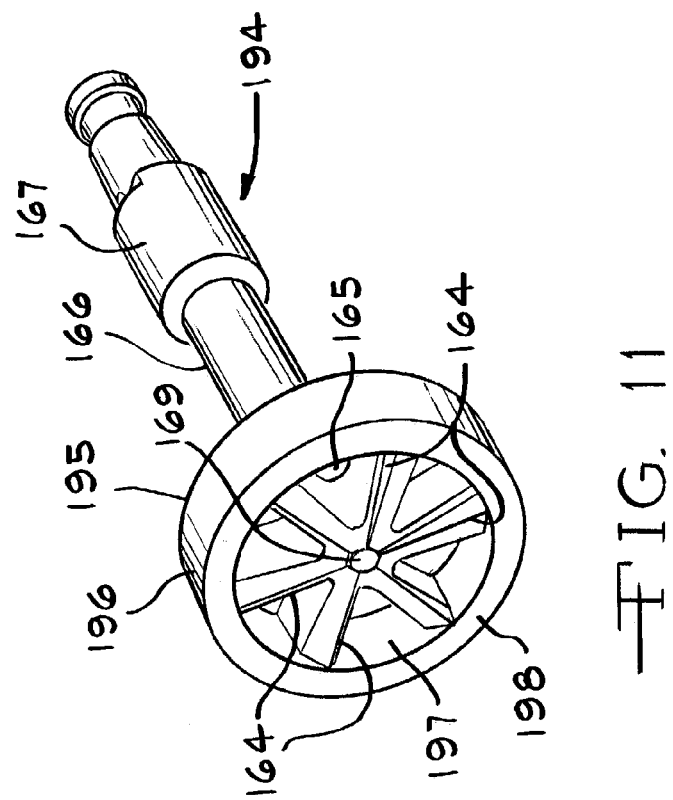
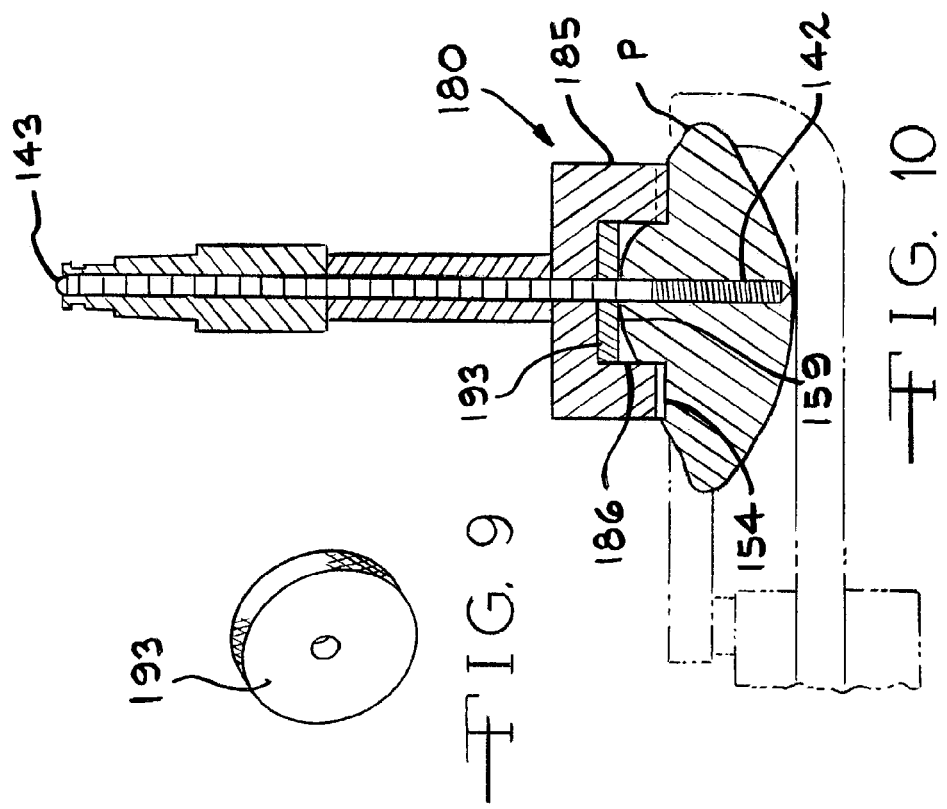

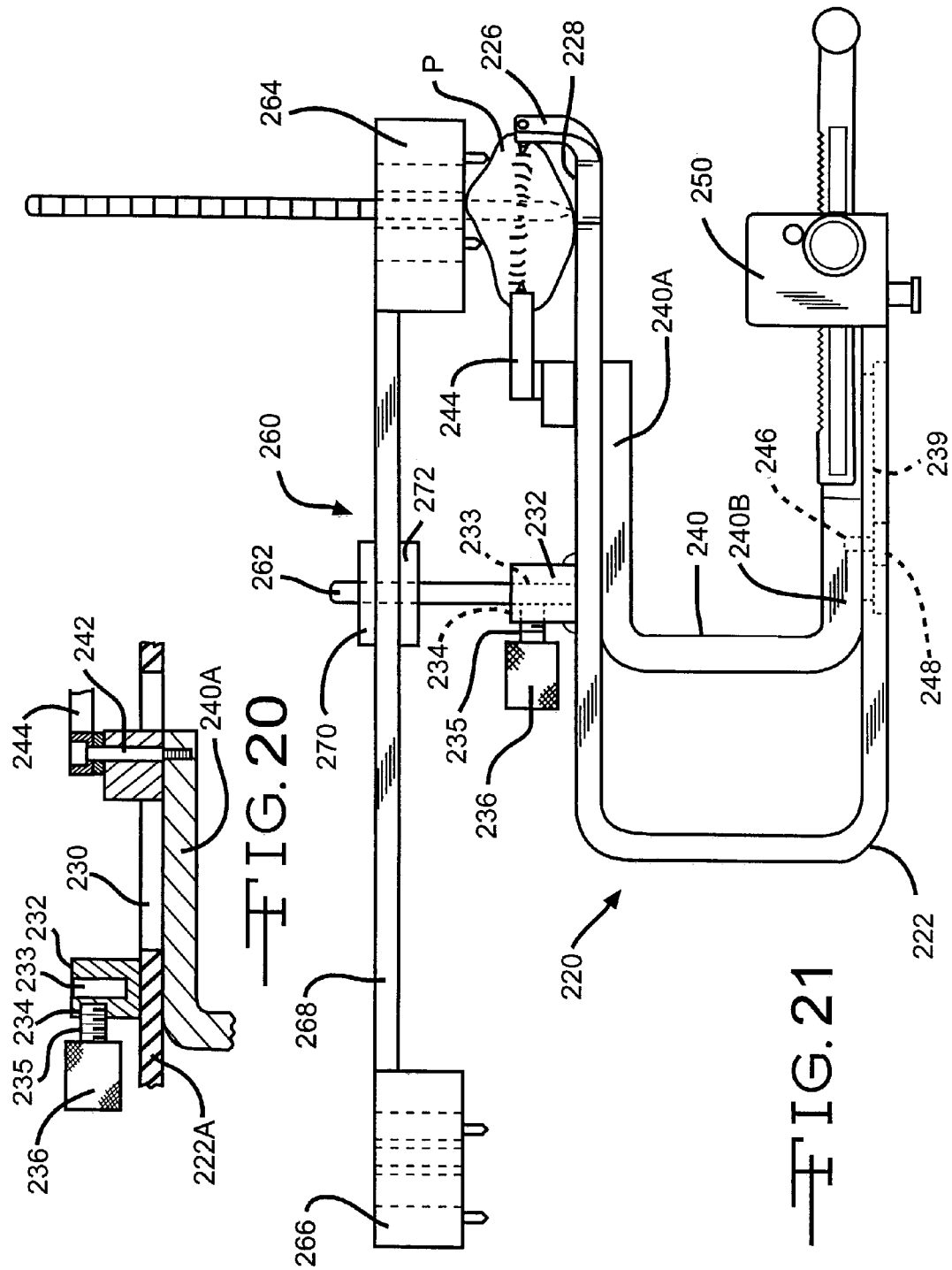

PATELLA RESECTION GUIDE

CROSS REFERENCE TO RELATED APPLICATION

This application is based upon and claims priority under Provisional Patent Application No. 60/359,631, filed Feb. 26, 2002.

SUMMARY OF THE INVENTION

The present patent application is directed to a patella resection guide for permitting precise measurement of the depth of a resection cut of the patella which may be used to support the patella and perform a precise resection cut from the dome portion without everting the patella.

BACKGROUND OF THE INVENTION

In performing knee surgery, it is frequently necessary to resect the patella preparatory to inserting a patellar prosthesis therein. Heretofore it has been necessary to evert the patella in order to have it positioned such that the resectioning can be effectively performed. The resection device of the present invention permits the patella to be resectioned without the necessity of everting it thereby simplifying the procedure and permitting it to be performed in a less invasive manner than was heretofore the case. Additionally, the resection device of the present invention permits other arthroplasty procedures to be performed without everting the patella including preparation of the distal end of the femur and the proximal end of the tibia.

BRIEF DESCRIPTION OF THE DRAWINGS

FIG. 1 is a plan view of a patella resection guide of the present invention.

FIG. 2 is an elevational view of the patella resection guide with a patella engaged.

FIG. 3 is a perspective view of a resection guide adjustment member.

FIG. 4 is a view similar to FIG. 1 with phantom lines showing movement of various components of the patella resection guide.

FIG. 5 is a plan view of a patella preparation guide for sizing a patella and guiding a drill in preparation of patella.

FIG. 6 is an elevational view of the patella preparation guide being used in combination with the patella resection guide.

FIG. 7 is an elevational view of a circumferential patella reamer being guided by the patella preparation guide.

FIG. 8 is a perspective view of the circumferential patella reamer of FIG. 7.

FIG. 9 is a perspective view of a spacer washer designed for possible use with the circumferential patella reamer of FIGS. 7 and 8.

FIG. 10 is a view showing the circumferential patella reamer in use in combination with the space washer.

FIG. 11 is a perspective view of a dome reamer for reaming the dome of a patella.

FIG. 20 is a sectional view taken through line 20-20 of FIG. 18.

FIG. 21 is an elevational view of the patella resection guide of FIGS. 17-20 used in combination with a modified combination sizing/alignment guide.

DETAILED DESCRIPTION OF THE PREFERRED EMBODIMENT

Figure 13:
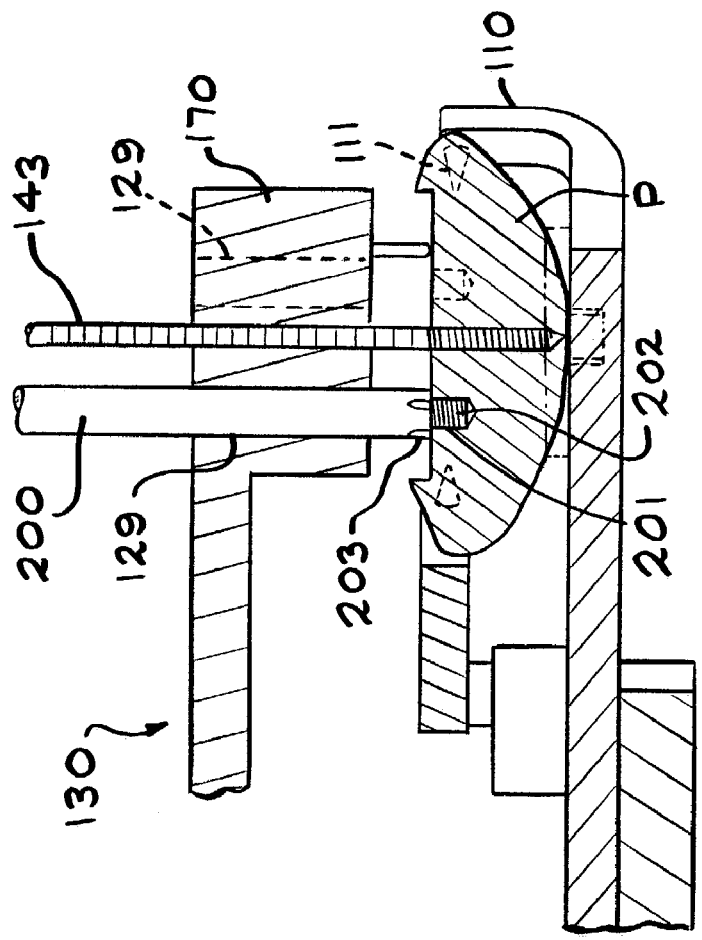
FIG. 13 is an elevational view of the patella preparation guide of FIG. 5 in use following reaming to guide the drilling of peg holes in the reamed surface of the patella.

FIGS. 1, 2 and 4 show plan and elevational views of a patella resection guide 100 permitting precise control of the depth of a resection cut of a patella P. The patella resection guide 100 includes a slide support 102 extending from a patella engagement end 103 to an opposing end 104 and having a forward central slot 105 and a rear slot 125.

The patella engagement end 103 extends longitudinally beyond the forward central slot 105 and is enlarged to extend laterally outwardly from the central axis of the forward central slot 105. A pair of upstanding tabs 110 are mounted in spaced-apart relationship on the enlarged patella engagement end 103. Supported on each of the tabs 110 is a tapered patella engagement pin 111 each of which points rearwardly and inwardly toward the axis of the forward central slot 105.

A secondary guide member 108 is secured to the slide support 102 for slideable movement relative thereto. The secondary guide member 108 includes a slide 112 on one side of the slide support 102 and a base 107 on the opposite side of the slide support 102. A support pin 106 is secured to the leading end of the slide 112 and extends through the slot 105 and through the base 107, extending upwardly from the base 107. A slideable cutting guide/support member 113 is pivotally mounted on the end of the support pin 106 for pivotal movement thereon.

The cutting guide/support 113 has a V-shaped configuration with a pair of patella engagement pins 111A extending toward the patella engagement end 103 and the patella engagement pins 111 supported on the tabs 110. One of the patella engagement pins 111A is located on one side of the support pin 106 and the other patella engagement pin 111A is on the opposite side of such support pin 106. Since the shape of a patella is not perfectly circular in the area to be gripped by the patella engagement pins 111 and 111A, the feature of permitting the cutting guide/support 113 to pivot about the support pin 106 assures that both of the patella engagement pins 111A, as well as both of the patella engagement pins 111, will engage the patella P.

FIG. 4 shows in phantom lines the possible range of pivotal movement of the cutting guide/support 113 as well as longitudinal movement of the secondary guide member 108 from a rearward disengaged position to a forward engaged position.

Extending upwardly from the opposite end of the slide 112 from the pivot pin 106 is a threaded screw 124 which extends through the rear slot 125. Encircling the rear slot 125 is a ledge 138 which is recessed from the upper surface of the slide support 102. A flat head cap screw 117 is engaged to the threaded screw 124 and rests upon the ledge 130 for sliding engagement therewith thereby providing support and guidance for that end of the slide 112.

Supported on the opposing end 104 of the slide support 102 is a base assembly 115 having a pair of gripping handles 116 extending from opposite sides thereof. Extending longitudinally through an opening in the base assembly 115 is a slideable plunger 118 having a gripping member 145 at the opposing end. The plunger 118 is connected to the end of the slide 112 adjacent the screw 124 by means of a connector which permits the plunger 118 to be rotated 90° from the position shown in FIGS. 1 and 2. The plunger 118 has a generally circular cross section configuration but with a series of ratchet teeth 119 facing downwardly as viewed in FIG. 2 and a recessed flat surface 146 positioned 90° therefrom. The ratchet teeth 119 and the recessed flat surface 146 extend longitudinally throughout a major portion of the plunger 118.

Housed within the enlarged base 115 is a pawl spring and pawl positioned to engage the ratchet teeth 119. The pawl and spring are so positioned within the base assembly 115 as to permit the plunger 118 to readily be moved forwardly toward the patella engagement end 103 (to the right as viewed in FIGS. 1 and 2) but to prevent rearward movement (movement to the left as viewed in FIGS. 1 and 2) when so engaged.

When it is desired to grip the patella P, the patella resection guide 100 is positioned such that the enlarged area adjacent the patella engagement end 103 supports the anterior side of the patella P and then is moved to a position at which the patella engagement pins 111 supported on the tabs 110 engage the central portion of the patella. The plunger 118 is then moved forward by pushing the gripping member 145 while holding the gripping handles 116 thereby causing the slide 112 to move toward the patella engagement end 103 and to grip the patella P with the patella engagement pins 111A carried on the slideable cutting guide 113. As previously discussed, the slideable cutting guide 113 is pivotally mounted on the support pin 106 to assure that the patella engagement pins 111A both engage the patella P notwithstanding any irregularities in the central portion of the patella P.

In order to release the ratchet teeth 119 from the pawl, there is provided a spring loaded lock release 123 which may be depressed to permit the plunger 118 to be rotated 90° to thereby disengage the ratchet teeth 119 from the pawl. Such rotation can be accomplished because the plunger 118 is rotatably secured to the slide 112. In order to prevent the plunger 118 from rotating when it is desired to be maintained in the patella gripping position shown in FIG. 2, the lock release 123 has a cylindrical surface which engages the recessed flat surface 146 of the plunger 118 when it is in the raised position thereby maintaining the plunger 118 in a fixed rotatable position. The lock release 123 is also provided with a short length adjacent the cylindrical surface having a recess on the side facing the plunger 118. When the lock release 123 is depressed, its recess becomes aligned with the plunger 118 thereby removing any contact of the lock release 123 with the recessed flat surface 146. The removal of contact by the lock release permits the plunger 118 to be rotated 90° to disengage the ratchet teeth 119 from the pawl. The plunger 118 may then be retracted to disengage the patella engagement pins 111A from the patella P.

If desired, the plunger 118 may have longitudinally extending line 147 embossed on the side opposite the ratchet teeth 119 in order to permit the surgeon to readily determine that the ratchet teeth 119 are facing in a position to engage the pawl. A similar line 147A may also be embossed in the upper surface of the enlarged base 115 to assist the surgeon in rotatable alignment.

Extending upwardly from a central portion of the slide support 102, between the forward central slot 105 and rear slot 125 is a support post 127 which may be used to assist in proper preparation of the patella.

Under one embodiment of the present invention, the patella resection guide as thus far described can be used for guiding a resectioning saw to cut the desired amount of the dome on the posterior surface of the patella. Thus, the sizing of the slideable cutting guide/support 113 and its positioning of its upper surface above the surface of the enlarged area of the slide support 102 adjacent the patella engagement end 103 upon which the anterior surface of the patella P rests is designed to leave a predetermined amount of patella P, 13 to 16 mm, between such upper surface and the supported portion of the anterior surface resting upon the enlarged end adjacent the end 103. As will be appreciated, in performing such resecting, the surgeon simply uses such upper surface of the slideable cutting guide/support 113 as a guide determining the plane of movement of the cutting saw.

In the event that the surgeon, upon engaging the patella P with the resection guide 100, ascertains that a lesser amount of bone should be resected from the dome of the patella, there is provided an adjustment member 114 (see FIG. 3) which may be positioned on the slideable cutting guide 113 and retained thereon by a pair of posts 114A engaging in a pair of recesses 113A of the slideable cutting guide. The posts 114A may be provided with C-shaped springs to permit their secure retention in the apertures 113A of the slideable cutting guide/support 113. The adjustment member 114 has a thickness equal to the reduction in the amount of bone to be resected from the patella, for example 3 mm.

The slideable cutting guide/support 113, as shown in FIGS. 1 and 2, is solid throughout its breadth and the surgeon uses its upper surface as a guide for the saw during the resecting of the patella P. Some surgeons prefer to have a slot through which the cutting saw may extend to guide the resecting of the patella. Accordingly, if desired, the slideable cutting guide/support 113 could be replaced by a slotted cutting guide/support.

Referring to FIGS. 5-13, there is shown additional components which may be used with the patella resection guide 100 in the resectioning process. For some applications, it is preferred to resect the patella by reaming rather than by use of a cutting saw.

Referring to FIGS. 5 and 6, there is shown a combination sizing/alignment guide 130 designed to be adjustably positioned on the support post 127 of the resection guide 100. The sizing/alignment guide 130 is shown as having a first enlarged head 170 at one end and a second enlarged head 171 at the opposing end joined together by an elongated arm 172. As viewed in plan (FIG. 5), the first enlarged head has a circular cross-sectional configuration of a certain diameter, for example 26 mm, and the second enlarged head 171 has a circular configuration with the different size, for example 28 mm in diameter. The elongated arm 172 has an elongated central slot 133. The sizing/alignment guide 130 is supported on the support post 127 by a lower adjustment member 175 positioned to engage the bottom of the arm 172 on opposite sides of the slot 133 and an upper adjustment member 174 positioned to engage the top of the arm 172 on opposite sides of the slot 133. The upper and lower adjustment members 174, 175 are circular and have a size approximating the breadth of the elongated arm 172.

The sizing/alignment guide 130 is useable both for drilling a hole in the central portion of the patella P either prior to any resecting of the dome portion thereof as shown in FIG. 6, or after resectioning if the surgeon elects to use a saw using the slideable cutting guide/support 113 as a guide as previously discussed. Accordingly, it is necessary that the upper and lower adjustment members 174, 175 have the capability of supporting the sizing alignment guide 130 on the support post 127 at a number of different elevations. This can be accomplished in any one of a number of mechanisms well known in the art such as threaded engagement between the members or clamps engaged to the upper and lower adjustment members 174, 175 for clamping such members to the support posts 127.

Each of the first enlarge head 170 and second enlarge head 171 is provided with a central passageway 126 for receiving and guiding a combination drill/guide rod 128 and three larger passageways 129 for receiving and guiding drills for drilling peg holes in the flat prepared surface (see FIG. 13) for receiving the pegs of a patellar prosthesis implant. The first and second enlarged heads 174 and 175 each extend downwardly below the lower surface of the arm 172 in order to provide a thickness sufficiently great that the central passageway 126 and the larger passageways 129 are long enough to accurately guide drills positioned therein.

Extending downwardly from each of the first and second enlarged heads 170 and 171 are three alignment pins 135 which may rest upon the resected surface of the patella P prior to drilling an aperture for positioning the drill guide 128 when the patella is resected with a saw as described with reference to FIG. 14 or for engaging the resected flat surface preparatory to drilling the peg holes following reaming as hereinafter discussed with reference to FIGS. 7-13.

The outside diameter of the enlarged head, for example, the first enlarged head 170 or the second enlarged head 171 of the sizing alignment guide 130 is selected based upon the diameter of the patellar prosthesis implant intended for the patella P, which size depends upon the size of the patient and the condition of the patella being prepared. The sizes of the enlarged heads 170, 171 may vary from 26 to 41 mm. The positioning of the apertures 129 for each size of enlarged head 170 or 171 is determined by the positioning of the peg lugs of the patellar prosthesis to be implanted. Although the sizing alignment guide 130 is shown as having two enlarged heads (first enlarged head 170 and the second enlarged head 171), this is done simply to reduce the number of sizing alignment guides 130 required for a set with varying sizes from 26 to 41 mm in diameter. Only a single enlarged head 170, 171 will be used for guiding the drilling and reaming in the preparation of a specific patella.

The support post 127 is positioned at right angles to the slide support 102. When the sizing/alignment guide 130 is so positioned on the support post 127, the pin alignment guide aperture 126 and the guide holes 129 for drilling the peg holes will be parallel to the support post 127. Preparatory to tightening the upper and lower adjustment members 174, 175 onto the support post 127, the sizing/alignment guide 130 may be moved to the right or to the left as shown in FIG. 6 by virtue of the support post extending through the slot 133, so that the pin alignment guide aperture 126 is properly positioned relative to the dome 159 of the patella P. A combination patella drill/guide pin 143 is affixed to a power drill at rounded end 140 and inserted through the guide hole 131. Upon drilling, the sharp trocar end 141 is advanced to a depth selected by the surgeon using the positioning of laser markings 139 on the drill/guide pin 143 for determining the depth. Preferably, the end of the drill/guide pin 143 will be provided with cutting threads 142 upwardly from the sharp trocar end 141 in order that the drill/guide pin 143 may be securely left in position in the newly drilled patella for use as a guide in the subsequent reaming and/or drilling steps.

With the drill/guide pin 143 engaged to the patella P, the sizing/alignment guide 130 may then be removed from the support posts 127 or rotated out of alignment with the patella P to provide room for a circumferential patella reamer to be positioned over the drill/guide pin 143. Although not shown in FIG. 7, the patella P remains engaged by the engagement pins 111, 111, 111A, 111A during the reaming operation. The resecting can be done without everting the patella P whether the resecting is done with a saw or with reamers.

As shown in FIGS. 7 and 8, there is provided a circumferential reamer 180 which includes an enlarged head 184 having an outer circumferential wall 185 which may vary in size depending upon the size the patella being resected and an inner cylindrical wall 186 which may be of a fixed diameter on the order of 10 millimeters plus or minus 1 millimeter. The distal end of the reamer 180 is provided with cutting teeth 187 which extend between the outer cylindrical wall 185 and inner cylindrical wall 186. The apex 187A of the cutting teeth 187 define the plane of the cut surface 154 of the partially resected patella P as shown in FIG. 7. The inner cylindrical wall 186 defines a cavity closed by an upper interior wall 188 disposed at right angles to the inner cylindrical wall 186. The depth of the cavity may be fixed at approximately 10 mm as measured from the apex 187A of the cutting teeth 187 to the upper interior end 188.

The circumferential reamer 180 is provided with a tubular member 189 attached to the head 184 and an enlarged power means gripping portion 190 engageable with a drill or other power means in a manner well known in the art. A central passageway 191 extends completely through the circumferential patella reamer 180 from the proximal end 192 to the upper interior wall 188 so that the circumferential patellar reamer 180 can be telescoped over the drill/guide pin 143 as shown in FIG. 7. As can also be seen in FIG. 7, the upper interior wall 188, upon reaming a circumferential portion of removed bone as shown by cut surface 154 will contact the dome 159 of the patella P to thereby limit the depth to which the circumferential removed bone at cut surface 154 is reamed.

In the event the surgeon determines that the size or condition of the patella being reamed is such that reaming to a depth of 10 mm as measured from the dome 159 of the patella P to the cut surface 154 would be excessive, he may insert a washer such as the washer 193 shown in FIGS. 9 and 10, into the inner cylindrical wall 186 and against the upper interior end 188 to reduce the effective cutting depth of the circumferential reamer 180 by a predetermined amount, for example, 2 mm for a washer 193 having a thickness of 2 mm or more for thicker washers.

Figure 12:
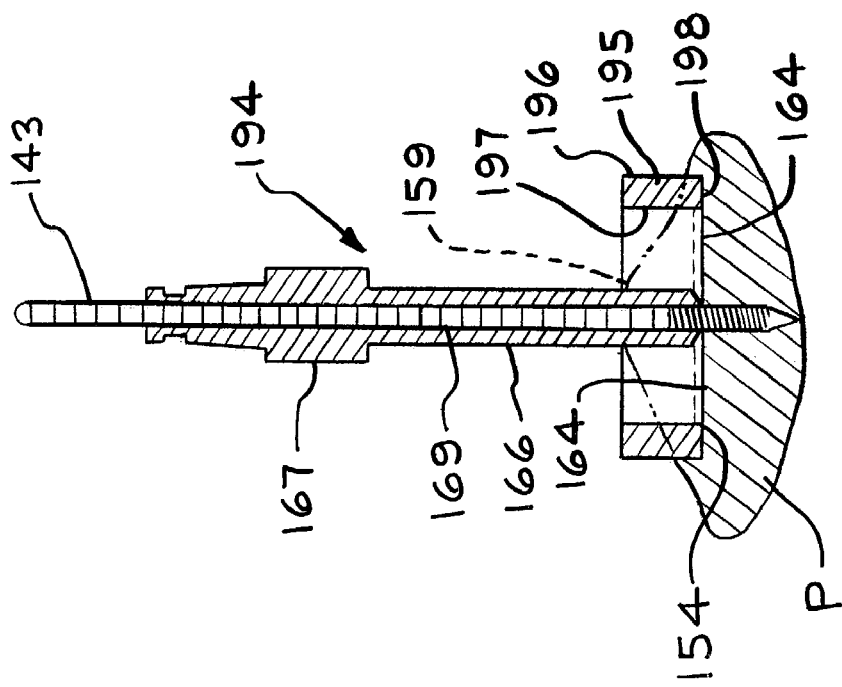
FIG. 12 is an elevational view of the dome reamer of FIG. 11 following reaming.

Referring to FIGS. 11 and 12, there is provided a finishing reamer 194 having an enlarged head 195 with an outer circumferential wall 196 having a diameter substantially the same as the diameter of the outer cylindrical wall 185 of the circumferential reamer 180 and an inner cylindrical wall 197 substantially the same size as the inner cylindrical wall 186 of the circumferential patella reamer 180. The finishing reamer 194 has a smooth distal end surface 198 extending between the outer cylindrical wall 196 and inner cylindrical wall 197. The breadth of the end surface 198 is no greater than the breadth of the circumferential cut surface 154 reamed by the circumferential reamer 180 and is preferably the same breadth. Positioned in the space defined by the inner cylindrical wall 197 are a series of cutting blades 164, six in number as shown in FIG. 11 which are separated by open portals 165 through which bone chips generated during the reaming process may be expelled.

A tubular shaft 166 and power engaging means 167 extend from the enlarged head 195. A cannulation passageway 169 extends completely through the finishing reamer 194.

Following reaming of the patella P with the circumferential patella reamer 180 and removal of the circumferential patella reamer from the drill/guide pin 143, the finishing reamer 194 is telescoped over the drill/guide pin 143. As shown in FIG. 12, the cutting surfaces 164 will then ream the dome 159 and adjacent portions of the patella P posterior side. The depth to which the dome 159 and adjacent surrounding bone will be reamed by the finishing reamer 194 will be limited by engagement of the smooth end surface 198 with the surface of the circumferential removed bone surface 154 reamed with the circumferential patella reamer 180.

Following completion of reaming with the finishing reamer 194 as shown in FIG. 12 and removal of the finishing reamer 194 from the drill/guide pin 143, the sizing/alignment guide 130 may then again be positioned on the support post 127 with the enlarged head 170 telescoped over the drill/guide pin 143. With the sizing/alignment guide 130 thus positioned, a drill 200 may then be successively guided through each of the peg alignment guide holes 129 to drill holes 201 for receiving the pegs of a patellar prosthesis implant to be positioned in the reamed surface of the patella P. Preferably the drill 200 has a shaft which is enlarged from the cutting end portion 202. Such enlarged shaft portion forms a distal shoulder 203 which engages the reamed surface of the patella P thereby limiting the depth to which the drill portion 202 can drill the peg hole 201.

Figure 14:
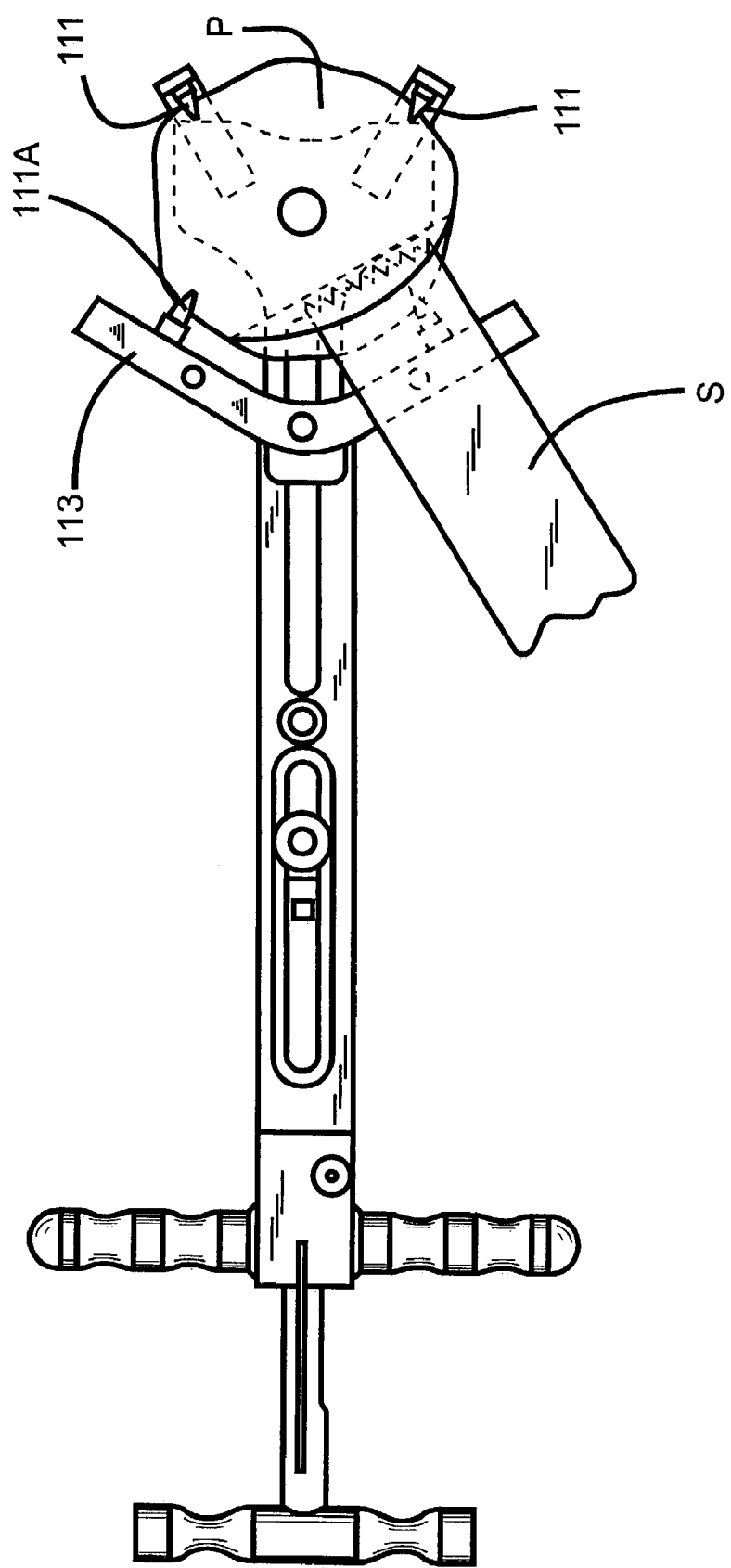
FIGS. 14 and 15 are views similar to FIGS. 1 and 2, respectively, showing the patella resection guide in use with the upper surface of the guide/support member determining the path of cutting movement of the saw through the patella.
Figure 15:
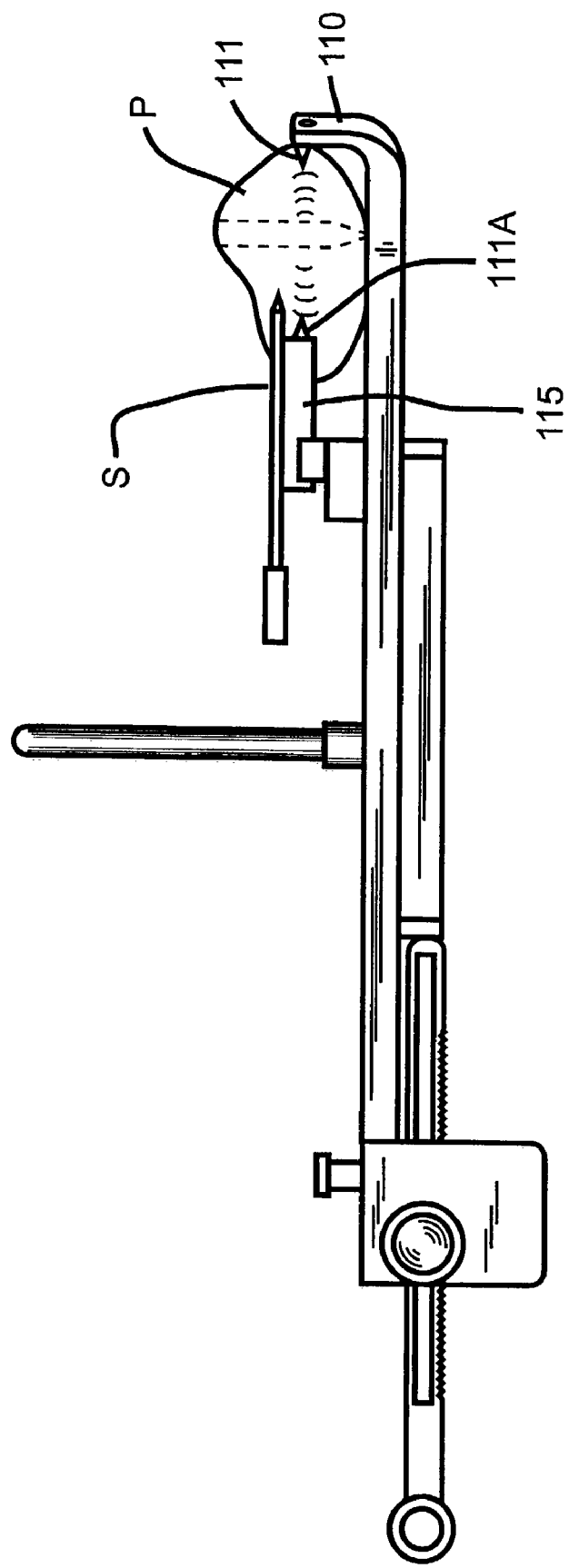

FIGS. 14 and 15 are views similar to FIGS. 1 and 2, respectively, showing the resecting of a patella P with a saw blade S while using the upper surface of the slideable cutting guide/support 113 as a guide.

Figure 16:
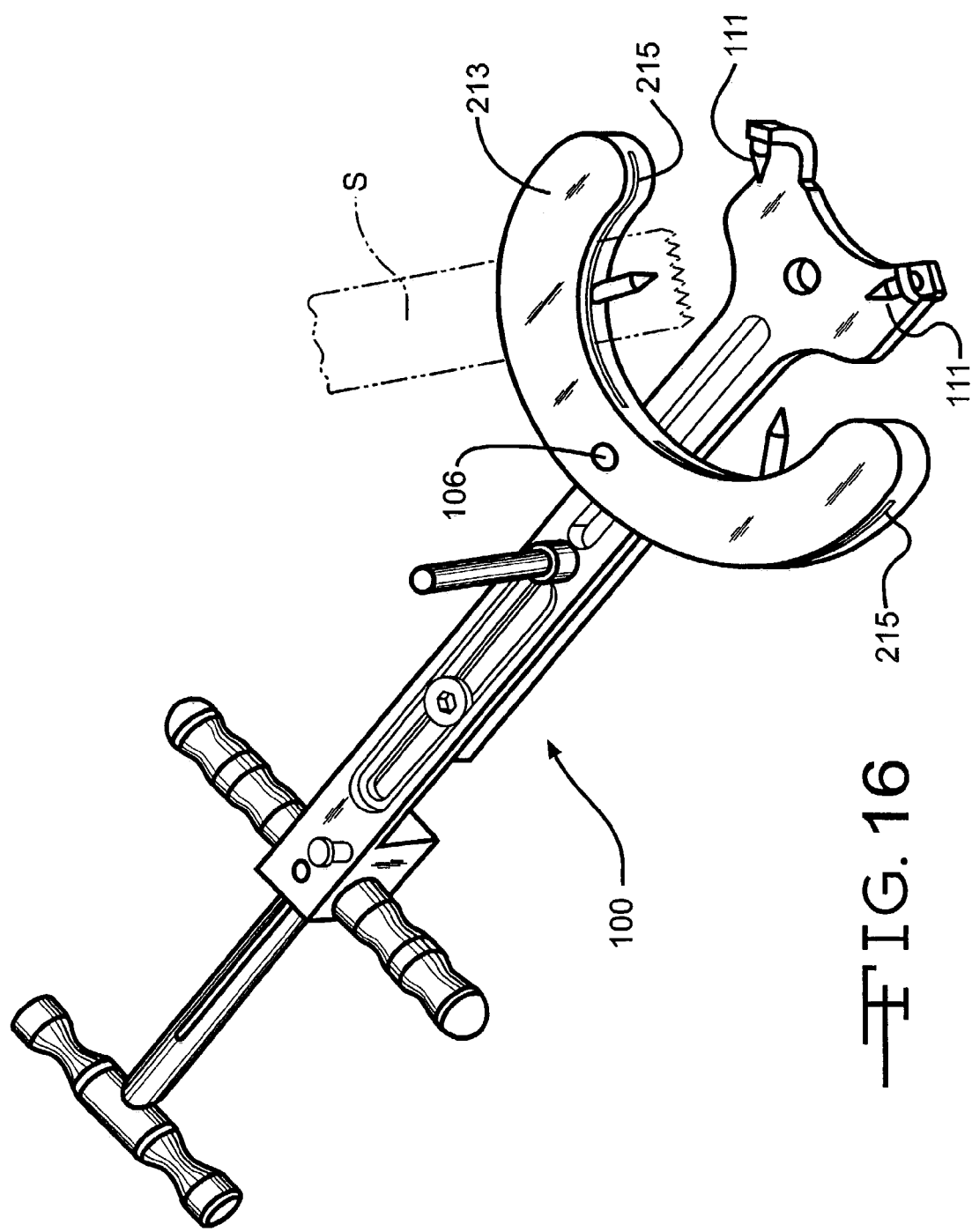
FIG. 16 is a perspective view of the patella resection guide modified to have a slotted guide/support member.
Figure 17:
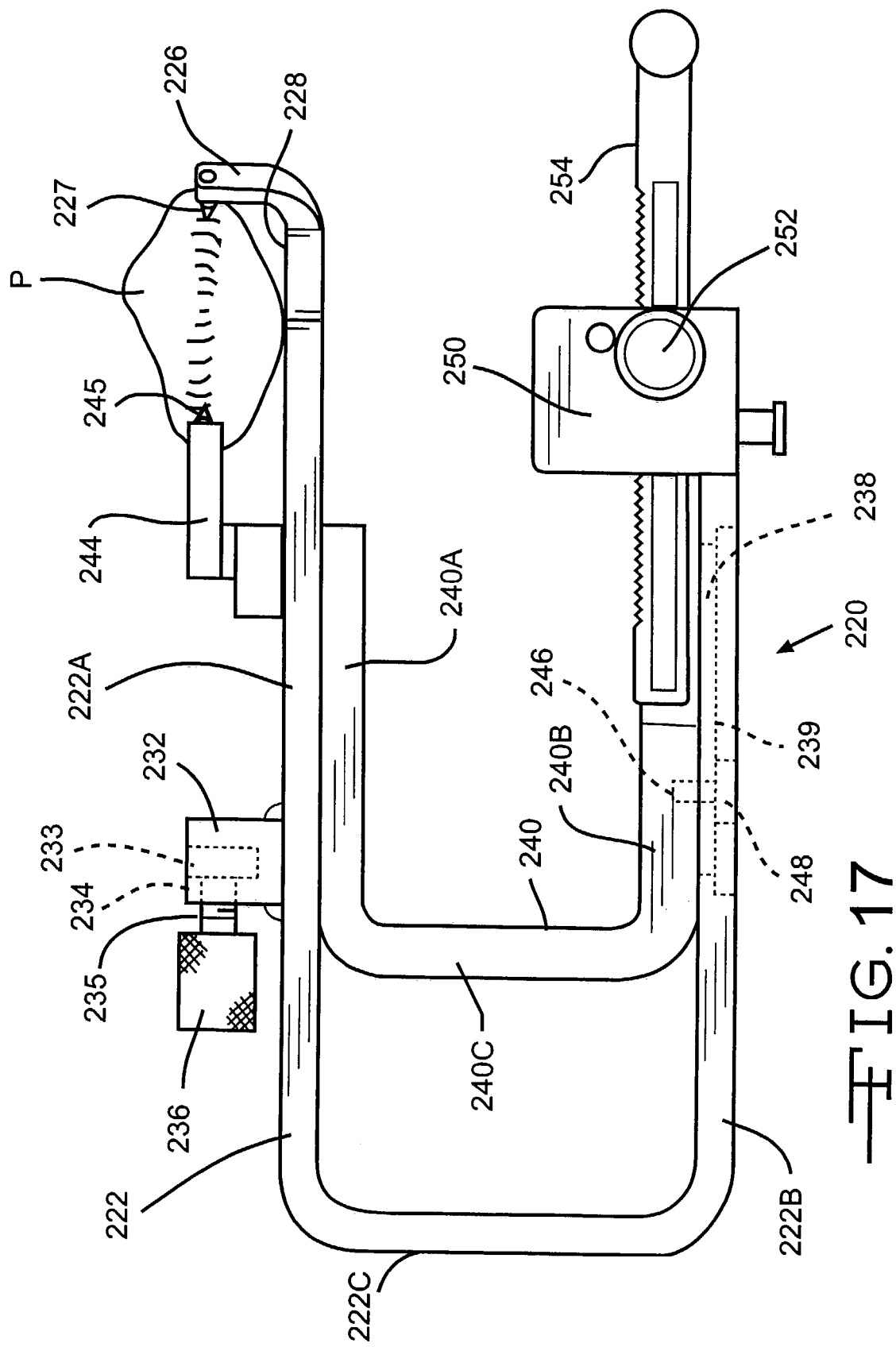
FIG. 17 is an elevational view of a modified embodiment of patella resection guide.
Figure 18:
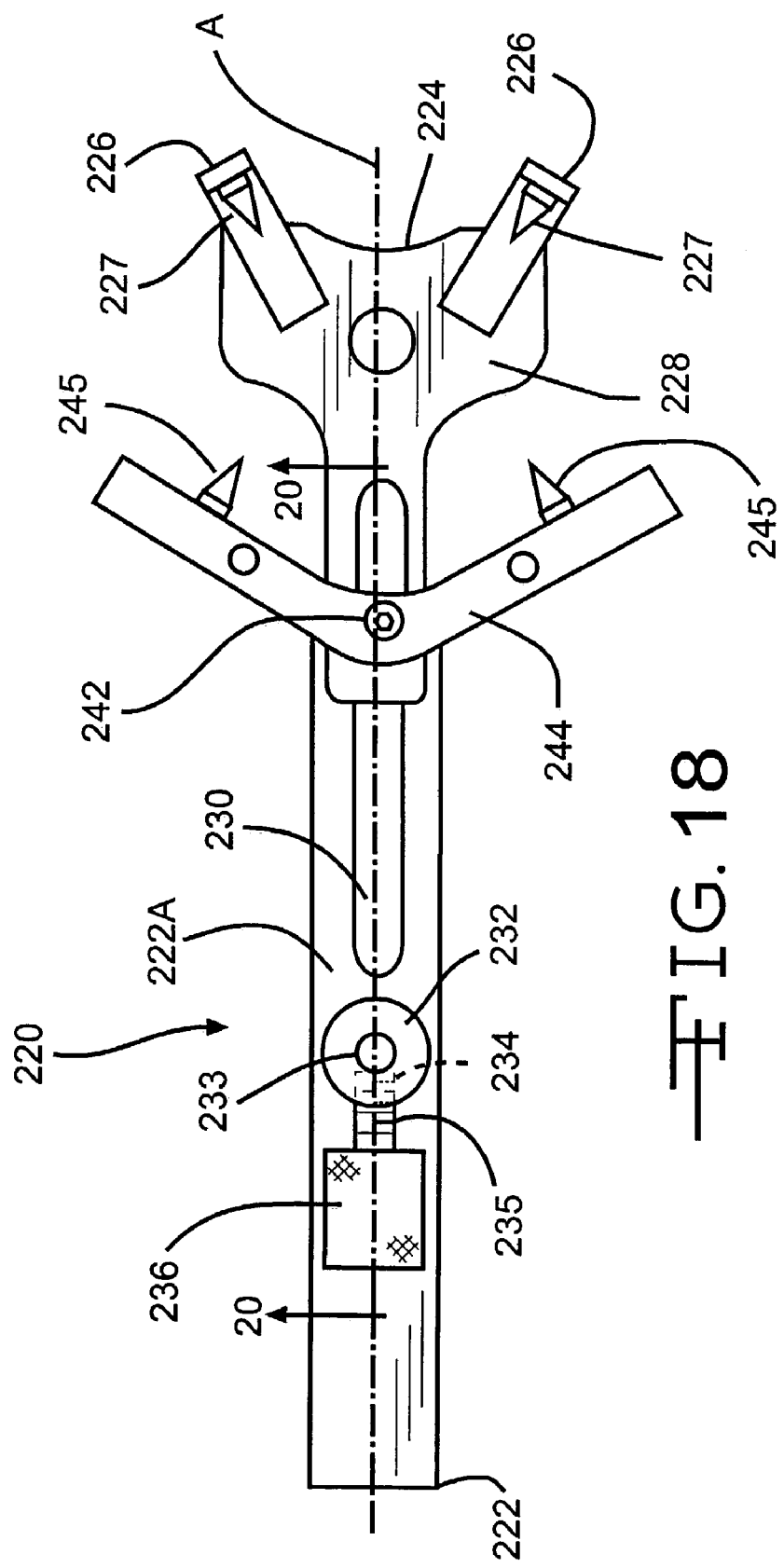
FIG. 18 is a plan view of the patella resection guide shown in FIG. 17.
Figure 19:
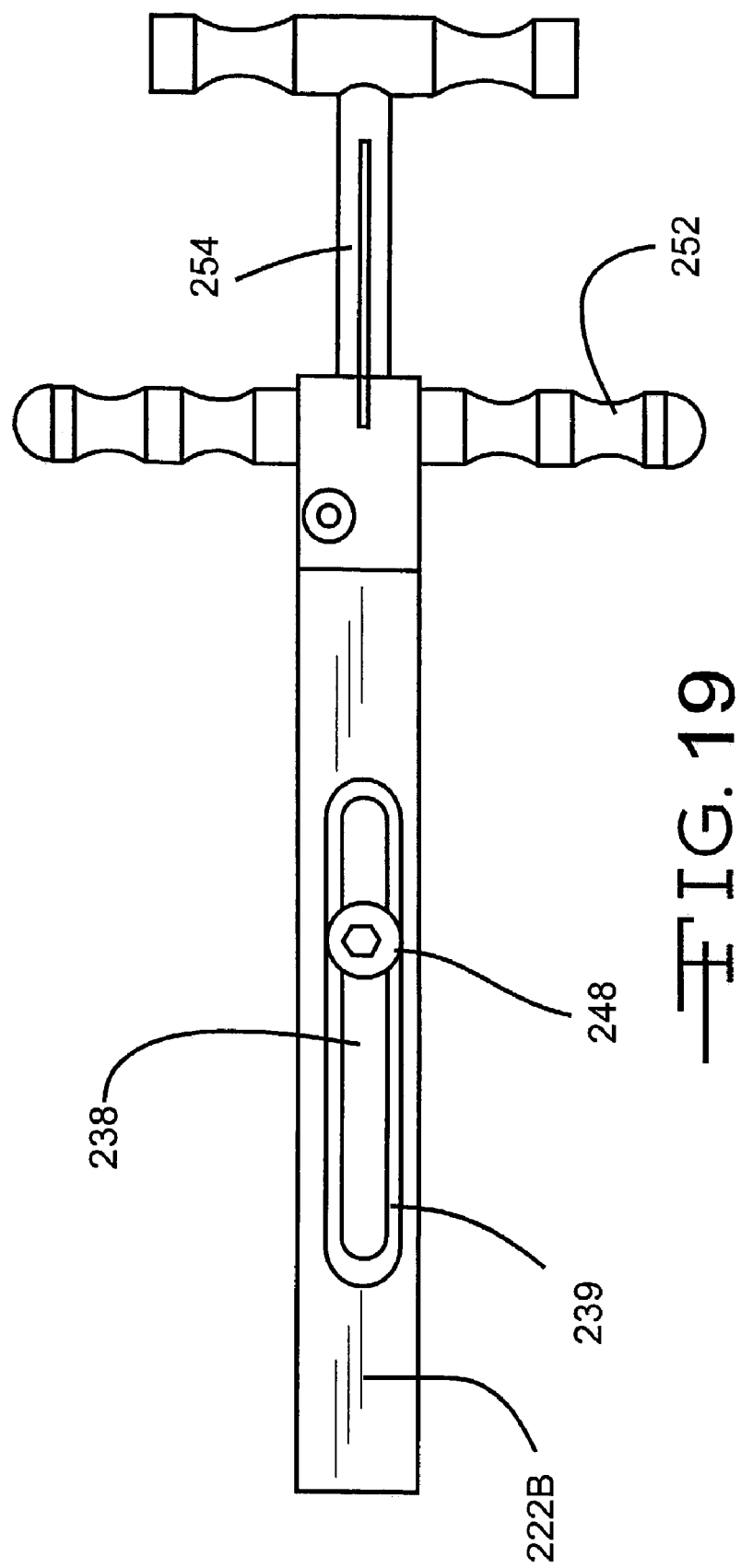
FIG. 19 is a bottom view of the patella resection guide shown in FIG. 17.

FIG. 16 shows a resection guide 100 which has a slotted cutting guide/support 213. The slotted cutting guide 213 has a pair of slots 215, one on each side of the support pin 106. In performing the resecting operation, the surgeon simply inserts the saw blade S through the slots, first one and then the other, to resect the patella.

Referring FIGS. 17-20, there is shown another embodiment of patella resection guide 220 which utilizes a shape under which the surgical assistant may engage and support the patella P and the resection guide 220 from the opposite side of the patient than in the embodiment of FIGS. 1 and 2. This positioning permits the surgeon to perform the resectioning of the patella P from a position to the left as viewed in FIGS. 17-19 without obstruction from such surgical assistant who may be positioned to the right as viewed in FIGS. 17-19. The modified patella resection guide 220 includes a slide support 222 and a slideable guide member 240. The slide support 222 has a U-shaped configuration as viewed in elevation in FIG. 17 including an upper leg 222A, a lower leg 222B, and a third leg 222C joining the first leg 222A and second leg 222B into a unitary structure. The upper leg 222A functions as a slide support and extends from its joinder with the third leg 222C to a patella engagement end 224 having a pair of upstanding tabs 226, each of which supports a patella engagement pin 227. Each of the patella engagement pins 227 extends at an angle inwardly toward the axis A and toward the third leg 222C. The upper leg 222A has an enlarged patella support surface 228 adjacent the patella engagement end 224 and an axially extending slot 230 extending from a position near the patella support surface 228 toward the third leg 222C.

Extending upwardly from the upper leg 222A is a post 232 having a recess 233 sized to receive and support a member to be hereinafter described. The post 232 is provided with a radially extending threaded aperture 234 in which is received a threaded stem 235 of a tightening handle 236. The lower leg 222B is also provided with an axially extending slot 238 having a widened area adjacent the lower surface defining a downwardly facing shoulder 239.

The slideable guide member 240 includes an upper leg 240A slidingly engaged to the lower surface of the upper leg 222A of the slide support 222 and a lower leg 240B slidingly engaged to the upper surface of the lower leg 222B and a third leg 240C joining the legs 240A and 240B. Secured to and extending upwardly from the leading end of the upper leg 240A is a support pin 242 (See FIG. 20) which extends through the slot 230 of the upper leg 222A of slide support 222 and has supported thereon a combination cutting guide and patella support member 244 which is similar to and functions in the same way as the cutting guide/support 113 of the embodiment of FIGS. 1 and 2. The cutting guide/support 244 is pivotally mounted on the support pin 242 and has a pair of patella engagement pins 245 extending therefrom. If desired, the cutting guide/patella support member 244 could be provided with slots such as the slots 215 of the embodiment of FIG. 16.

The lower leg 240B is slideably engaged to the upper surface of the lower leg 222B of the slide support 222. The lower leg 240B has a pin 246 extending downwardly therefrom through the slot 238. The pin 246 has an enlarged head 248 which engages the shoulder 239.

Supported on the end of the lower leg 222B of the slide support 222, at the end opposite the leg 222C, is a base assembly 250 similar to the base assembly 115 of the embodiment of FIGS. 1 and 2 including a pair of gripping handles 252. Secured to the end of the lower leg 240B and extending longitudinally through an opening in the base assembly 250 is a slideable plunger 254 similar to the slideable plunger 118 of the embodiment of FIGS. 1 and 2.

When it is desired to grip the patella P, the patella resection guide 220 is positioned such that the anterior surface of the patella P rests on the support surface 228. The resection guide 220 is moved to a position at which the patella engagement pins 227 supported on the upstanding tabs 226 engage the central portion of the patella P. The slideable plunger 254 is then moved in a direction (to the right as viewed in FIGS. 17, 18 and 19) which moves the cutting guide/patella support 244 toward the patella P to a position at which the patella engagement pins 245 engage the patella P. When so engaged, the resecting of the patella P according to one or more of the procedures previously described may be performed.

Referring to FIG. 21, there is shown a combination sizing/alignment guide 260 which is used for similar purposes as the sizing alignment guide 130 of the embodiment of FIGS. 5 and 6. As such, it includes first enlarged head 264 and a second enlarged head 266 at opposing ends of an elongated arm 268 having an elongated slot. Under this embodiment, however, the modified sizing/alignment guide 260 has a support pin 262 engaged thereto and extending through a longitudinal slot similar to the slot 133 of the embodiment of FIG. 5. The sizing/alignment guide 260 is supported on the pin 262 by a pair of enlarged engagement nuts 270 and 272 which are threadedly engaged to the upstanding pin 262. Adjustment of the engagement nuts 270 and 272 on the pin 262 to loosen their engagement with the elongated arm 268 permits the sizing/alignment guide 260 to move longitudinally, rotationally and upwardly or downwardly on the pin 262 in order that the desired enlarged head 264 or 266 may be properly engaged to the patella P.

The pin 262 may be supported in the cavity 233 of the post 232. Tightening of the handle 236 and its threaded stem 235 will firmly engage the pin 262 in the cavity 233.

If desired, the adjustment member 114 could also be provided with slots through which the saw could be guided.

The above detailed description of the present invention is given for explanatory purposes. It will be apparent to those skilled in the art that numerous changes and modifications can be made without departing from the scope of the invention.

We claim:

1. A method for preparing a patella to receive a patellar prosthesis, said patella having an anterior surface, an opposing posterior surface with a dome and a peripheral edge between said anterior surface and said posterior surface, comprising the steps of:
    (a) engaging said anterior surface;
    (b) engaging said peripheral edge at spaced apart portions;
    (c) cutting a portion of said patella adjacent said posterior surface;
    (d) positioning a guide surface for a cutting tool posteriorly of said spaced apart portions and engaging said guide surface with said cutting tool during step (c); and
    (e) cuffing said patella without everting said patella.

2. The method according to claim 1 further including the steps of providing a sizer having an edge defining at least a portion of a circle, said sizer having a central aperture, selecting a sizer having an edge size based upon the peripheral size of the cut portion of said patella, positioning said sizer on said cut portion and drilling a recess in said patella using said central aperture to guide said drilling.

3. The method according to claim 2 further including the step of maintaining said patella in an uneverted position throughout said cutting and drilling.

4. The method according to claim 1 wherein said cutting includes the steps of
    (a) providing a first reamer having (i) a circular cutting portion defining an outer diameter and an inner diameter and (ii) a central stop surface recessed from said cutting portion;
    (b) rotating said reamer while said cutting portion is engaged to said posterior surface; and
    (c) engaging said dome with said central stop surface to limit the depth to which said cutting portion may cut said patella.

5. The method according to claim 4 wherein said reamer has a cannulation passageway extending through said central stop surface and further including the steps of
    (a) providing a bone drill;
    (b) drilling a hole in said patella with said bone drill;
    (c) positioning said reamer on said bone drill with said bone drill extending through said passageway; and
    (d) using said bone drill as a guide while rotating said reamer.

6. The method according to claim 4 further including the steps of:
    (a) providing a second reamer, said second reamer having (i) a central cutting portion and (ii) a circumferential stop surface sized to engage the portion of said patella cut by said first reamer;
    (b) rotating said second reamer to cut said patella; and
    (c) engaging said circumferential stop surface to said portion of said patella cut by said first reamer to limit the depth of reaming by said central cutting portion.

7. The method according to claim 6 wherein said second reamer has a central passageway and further including the step of positioning said second reamer with a drill extended through said central passageway prior to rotating said second reamer.

8. The method according to claim 4 further including the step of positioning a washer against said central stop surface prior to rotating said reamer.

9. The method according to claim 4 further including the steps of (a) providing a guide member having (i) a movable member for engaging said peripheral edge at least one of said spaced apart portions, (ii) fixed means for engaging one or more additional spaced apart portions and (iii) a support member spaced from said fixed means; (b) moving said movable member toward said fixed means to engage and hold said patella by said movable member and said fixed means; and (c) providing a sizer having a guide passageway; (d) positioning said sizer on said support member with said guide passageway positioned over a central portion of said patella; (e) drilling at least one recess in said patella using said guide passageway to guide said drilling; (f) providing a first reamer having (i) a circular cutting portion defining an outer diameter and an inner diameter and (ii) a central stop surface recessed from said cutting portion; (g) rotating said reamer while said cutting portion is engaged to said posterior surface; and (h) engaging said dome with said central stop surface to limit the depth to which said cutting portion may cut said patella.

10. The method according to claim 1 further including the steps of (a) providing a guide member having (i) a movable member for engaging said peripheral edge at least one of said spaced apart portions, (ii) fixed means for engaging said peripheral edge at one or more additional spaced apart portions and (iii) a support member spaced from said fixed means; (b) moving said movable member toward said fixed means to engage and hold said patella by said movable member and said fixed means; (c) providing a sizer having a guide passageway; (d) positioning said sizer on said support member with said guide passageway positioned over a central portion of said patella; (e) drilling with a bone drill at least one recess in said patella while using said guide passageway to guide said drill; (f) providing a first reamer having (i) a circular cutting portion defining an outer diameter and an inner diameter and (ii) a central stop surface recessed from said cutting portion; (g) rotating said reamer while said cutting portion is engaged to said posterior surface; and (h) engaging said dome with said central stop surface to limit the depth to which said cutting portion may cut said patella.

11. The method according to claim 10 wherein said drill is positioned in said one recess and said first reamer is provided with a cannulation passageway and further including the step of positioning said reamer on said bone drill with said bone drill extending through said cannulation passageway prior to rotating said reamer.

12. The method according to claim 10 further including the steps of:
    (a) providing a second reamer, said second reamer having (i) a central cutting portion and (ii) a circumferential stop surface sized to engage the portion of said patella cut by said first reamer;
    (b) rotating said second reamer to cut said patella; and (c) engaging said circumferential stop surface to said portion of said patella cut by said first reamer to limit the depth of reaming by said central cutting portion.

13. A method for preparing a patella to receive a patellar prosthesis, the patella having an anterior surface, an opposing posterior surface with a dome and a peripheral edge between the anterior surface and the posterior surface, the method comprising the steps of:
provinding a patella resection guide having a guide member, the guide member including a movable member for engaging the peripheral edge at spaced apart portions and a guide surface for a cutting tool;
providing fixed means for engaging the peripheral edge at one or more additional spaced apart portions;
moving the movable member toward the fixed means to engage the patella peripheral edge with the movable member and the fixed means by directing an engaging force in a direction substantially perpendicular to an anterior-posterior direction of the patella; and
moving the cutting tool along the guide surface while cuffing the patella without everting the patella.

14. The method according to claim 13 wherein said guide surface defines a portion of a guide slot and further including the step of extending said cutting tool through said guide slot.

15. A method for preparing a patella to receive a patellar prosthesis, said patella having an anterior surface, an opposing posterior surface with a dome and a peripheral edge between said anterior surface and said posterior surface, comprising the steps of:
  (a) engaging said anterior surface;
  (b) engaging said peripheral edge at spaced apart portions; and
  (c) cutting a portion of said patella adjacent said posterior surface by
  (d) providing a first reamer having (i) a circular cutting portion defining an outer diameter and an inner diameter, (ii) a central stop surface recessed from said cutting portion, and a cannulation passageway extending through said central stop surface
  (e) rotating said reamer while said culling portion is engaged to said posterior surface;
  (f) engaging said dome with said central stop surface to limit the depth to which said cutting portion may cut said patella;
  (g) providing a guide member having (i) a movable member for engaging said peripheral edge at least one of said spaced apart portions, (ii) fixed means for engaging one or more additional spaced apart portions and (iii) a support member spaced from said fixed means;
  (h) moving said movable member toward said fixed means to engage and hold said patella by said movable member and said fixed means;
  (i) providing a sizer having a guide passageway;
  (j) positioning said sizer on said support member with said guide passageway positioned over a central portion of said patella;
  (k) drilling at least one recess in said patella using said guide passageway to guide said drilling;
  (l) providing a first reamer having (i) a circular culling portion defining an outer diameter and an inner diameter and (ii) a central stop surface recessed from said culling portion;
  (m) rotating said reamer while said cutting portion is engaged to said posterior surface
  (n) engaging said dome with said central stop surface to limit the depth to which said cutting portion may cut said patella;
  (o) providing a second reamer, said second reamer having (i) a central cutting portion and (ii) a circumferential stop surface sized to engage the portion of said patella cut by said first reamer;
  (p) rotating said second reamer to cut said patella; and
  (q) engaging said circumferential stop surface to said portion of said patella cut by said first reamer to limit the depth of reaming by said central cutting portion.

* * * * *